US011986499B2

(12) United States Patent
Rubin et al.

(10) Patent No.: US 11,986,499 B2
(45) Date of Patent: May 21, 2024

(54) TREATMENT AND PREVENTION OF NEUROPATHOLOGY ASSOCIATED WITH NEURODEGENERATIVE DISEASES

(71) Applicant: ILiAD Biotechnologies, LLC, Weston, FL (US)

(72) Inventors: Keith Rubin, Fort Lauderdale, FL (US); Steven Glazer, Weston, CT (US); Marina Lynch, Dublin (IE); Kingston Mills, Dublin (IE)

(73) Assignee: ILiAD Biotechnologies, LLC, Weston, FL (US)

( * ) Notice: Subject to any disclaimer, the term of this patent is extended or adjusted under 35 U.S.C. 154(b) by 10 days.

(21) Appl. No.: 17/455,173

(22) Filed: Nov. 16, 2021

(65) Prior Publication Data

US 2022/0152123 A1 May 19, 2022

Related U.S. Application Data

(60) Provisional application No. 63/114,909, filed on Nov. 17, 2020.

(51) Int. Cl.
*A61K 35/74* (2015.01)
*A61P 25/28* (2006.01)

(52) U.S. Cl.
CPC .............. *A61K 35/74* (2013.01); *A61P 25/28* (2018.01)

(58) Field of Classification Search
CPC ................................ A61K 35/74; A61P 25/28
See application file for complete search history.

(56) References Cited

U.S. PATENT DOCUMENTS

| | | |
|---|---|---|
| 9,119,804 B2 | 9/2015 | Locht et al. |
| 9,528,086 B2 * | 12/2016 | Locht ..................... A61P 11/06 |
| 9,655,959 B2 | 5/2017 | Alonso et al. |
| 9,730,995 B2 | 8/2017 | Locht et al. |
| 10,682,377 B2 | 6/2020 | Solans et al. |
| 2014/0271690 A1 | 9/2014 | Wang |

FOREIGN PATENT DOCUMENTS

| | | |
|---|---|---|
| EP | 1184459 | 3/2002 |
| WO | 2019077028 | 4/2019 |
| WO | 2020049133 | 3/2020 |

OTHER PUBLICATIONS

Patrick, Kristin L., et al. "Exploring the "multiple-hit hypothesis" of neurodegenerative disease: bacterial infection comes up to bat." Frontiers in Cellular and Infection Microbiology 9 (2019): 138. (Year: 2019).*
Morris, John C., et al. "Mild cognitive impairment represents early-stage Alzheimer disease." Archives of neurology 58.3 (2001): 397-405. (Year: 2001).*
National Institute on Aging "Alzheimer's Disease Genetics Fact Sheet". Retrieved from https://www.nia.nih.gov/health/alzheimers-disease-genetics-fact-sheet#:~: text=APOE%20%CE%B54% 20increases%20risk%20for,to%205%25%20carry%20two% 20copies on Apr. 12, 23. (Year: 2023).*
Molloy, D. William et al.: "A multicenter, blinded, randomized, factorial controlled trial of doxycycline and rifampin for treatment of Alzheimer's disease: the DARAD trial," Int J Geriatr Psychiatry, 2013: No. 28:463-470.
Rubin, Keith et al.: "The pertussis hypothesis: Bordetella pertussis colonization in the pathogenesis of Alzheimer's disease," Immunobiology, 2016:1-13.
Sochocka, Marta et al.: "The infectious etiology of Alzheimer's Disease," Current Neuropharmacology, 2017, No. 15: 996-1009.
Locht, Camille: "Molecular aspects of Bordetella pertussis pathogenesis," Internatl Microbiol, 1999, vol. 2:137-144.
Williams, Margaret M. et al: "Bordetella pertussis Strain Lacking Pertactin and Pertussis Toxin," Emerging Infectious Diseases, Feb. 2016, vol. 22, No. 2: 319-322.
Schnoeller, Corinna et al.: "Attenuated Bordetella pertussis Vaccine Protects against Respiratory Syncytial Virus Disease via an IL-17-Dependent Mechanism," American Journal of Respiratory and Critical Care Medicine, Jan. 15, 2014, vol. 189, No. 2:194-202.

* cited by examiner

*Primary Examiner* — Robert J Yamasaki
*Assistant Examiner* — Trevor Kane
(74) *Attorney, Agent, or Firm* — Stanley A. Kim

(57) ABSTRACT

Administering a live, attenuated *Bordetella pertussis*-based vaccine to a subject at risk for developing a neurodegenerative disease featuring Aβ brain plaques can prevent or reduce the amount of Aβ brain plaques that would have developed in the subject without such treatment.

10 Claims, 2 Drawing Sheets

Figure 1:
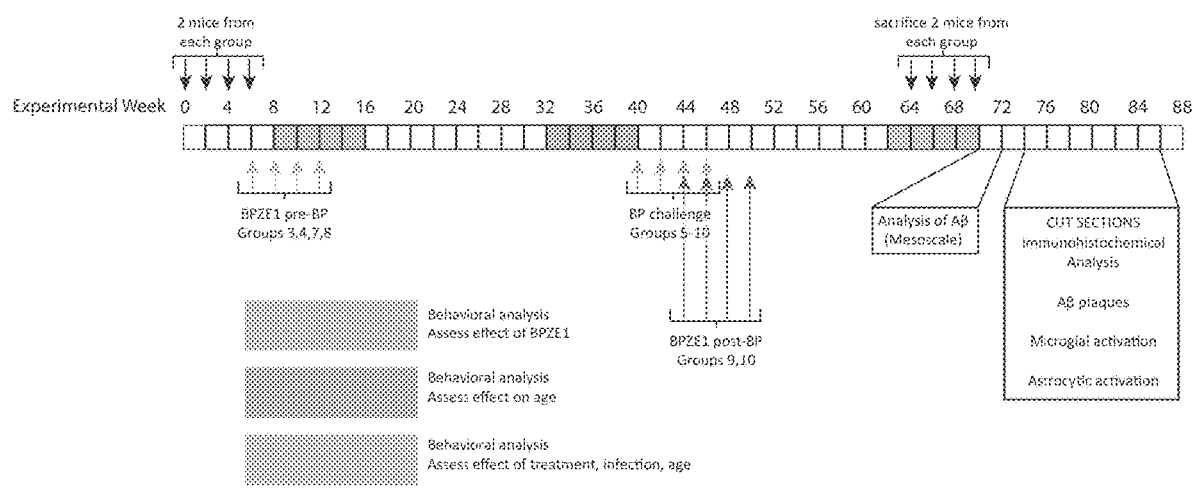
Figure 2:
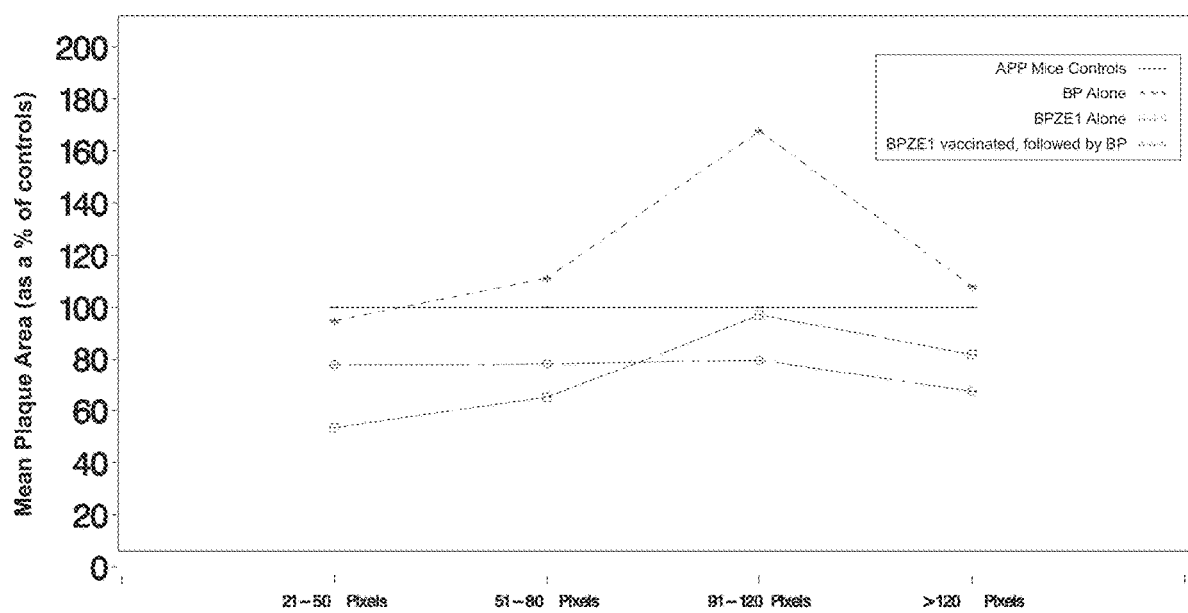

TREATMENT AND PREVENTION OF NEUROPATHOLOGY ASSOCIATED WITH NEURODEGENERATIVE DISEASES

CROSS-REFERENCE TO RELATED APPLICATION

The present application claims the priority of U.S. provisional patent application Ser. No. 63/114,909 filed on Nov. 17, 2020.

STATEMENT AS TO FEDERALLY SPONSORED RESEARCH

Not applicable.

FIELD OF THE INVENTION

This disclosure relates generally to the fields of microbiology, vaccinology, neurology, and medicine. More particularly, this disclosure relates to preventing or reducing neuropathology associated with neurodegenerative diseases such as Alzheimer's Disease (AD) in a subject by preventing or reducing *Bordetella pertussis* (BP) clinical infection or subclinical BP colonizing infection in the subject.

BACKGROUND

AD is a neurodegenerative disorder characterized by slowly progressive cognitive and behavioral impairment in those with intracellular cerebral neurofibrillary tangles (NFTs) composed of abnormal tau protein, and extracellular plaques composed of amyloid-β (Aβ) peptide. Current treatments only help with the symptoms of the disease, and, despite significant effort, no treatments to stop or reverse the progression of the disease have been approved.

The causes and progression of AD are not well understood. Most cases of AD are sporadic and occur after age 65. The risk of developing the disease is best predicted by age. Genetics also plays an important role in susceptibility to AD. Mutations at several distinct genetic loci have been identified that appear to influence initiation and progression of AD. These mutations are found in the genes, including those encoding amyloid precursor protein, presenilin I, and presenilin II, and Apolipoprotein E allotypes. For example, the presence of an APOE epsilon-4 allele in a subject imparts a relative risk for developing the disease of 30 times that of non-carriers, and 3.7 times that of epsilon-3/epsilon-4 heterozygotes (Myers, R. H., et al. "Apolipoprotein E element 4 association with dementia in a population-based study: The Framingham Study," *Neurology* 46.3 (1996): 673-677.) The relationship of other factors (e.g., low hormone levels, metal exposure) and AD is under study, but no definite causal links have been established.

For decades, most experts believed that pathologically produced amyloid beta (Aβ) fibrils and plaques accumulate in brain tissue which activates microglia and astrocytes, leading to brain neuroinflammation and eventually synaptotoxicity and neuronal death. Others have proposed that systemic inflammatory disease may drive neurodegeneration in AD and that prions might cause AD.

Although mostly shunned by the scientific community, another hypothesis is that AD is caused by microbial infection. A clinical trial aimed at clearing *Chlamydia pneumoniae* colonization in subjects with mild to moderate AD found there was no statistically significant benefit in the groups treated with antibiotics in comparison with the group administered placebo. Molloy et al., Int J Geriat Psychiatry, 28:463-70, 2013. Other microorganisms proposed to contribute to AD pathology include human herpesviruses 1-6, Hepatitis C virus, *Helicobacter pylori, Borrelia burgdorferi, Treponema pallidum, Porphyromonas gingivalis, Fusobacterium nucleatum, Prevotella intermedia, Candida albicans*, and *Toxoplasma gondii*. Sochocka et al., Curr Neuropharmacol, 15:996-1009, 2017. Still, the concept that AD has an infectious origin remains controversial because no specific pathogen has been conclusively proven to cause AD.

SUMMARY

It was discovered that administering a live, attenuated BP-based vaccine to a subject at risk for developing a neurodegenerative disease featuring Aβ brain plaques can prevent or reduce the amount of Aβ brain plaques that would have developed in the subject without such treatment. Notably, the vaccine-mediated protective responses were observed even in subjects not later infected with a pathogenic strain of BP.

Based on these discoveries, described herein are methods for preventing or treating a pathological feature of a neurodegenerative disease such as AD in a subject having or at risk for developing that disease by administering to a subject an agent which (a) prevents or reduces subclinical BP colonizing infection or BP clinical infection, or (b) neutralizes a BP toxin which causes or contributes to a pathological feature of a neurodegenerative disease such as AD. Also described herein are methods for preventing or reducing β-amyloid plaque in the brain of a subject having or at risk for developing AD. The latter methods include a step of administering to the subject a therapeutically effective amount of a live, attenuated *Bordetella pertussis* strain (e.g., in a pharmaceutically acceptable composition or vaccine) which is able to colonize the subject and induce a protective response in the subject that reduces the amount of β-amyloid plaque that would have formed or would have been present in the brain of the subject if the subject were not administered the composition.

The agent can be a live, attenuated *Bordetella pertussis* strain which is able to induce a non-virulent BP subclinical colonizing infection in the subject (e.g., a respiratory tract colonizing infection) and induce a protective response in the subject that prevents or reduces the pathological features of the neurodegenerative disease. The live attenuated *Bordetella pertussis* strain can be one that includes a mutated pertussis toxin gene, a deleted or mutated dermonecrotic gene, and a heterologous ampG gene which replaces the native BP ampG gene (e.g., a BPZE1 strain deposited with the Collection Nationale de Culture Microorganismes (C.N.C.M.) on Mar. 9, 2006, under accession number 1-3585).

The neurodegenerative disease can be one characterized by the presence of beta amyloid plaques in the brain of the subject, and the step of administering to the subject the vaccine can result in a protective response that reduces or prevents Aβ plaque formation in the brain of the subject.

In the methods described herein, the subject can be one diagnosed with, or at risk for developing, Alzheimer's disease, or one with mild cognitive impairment. The subject can also be one having mutations in at least one of the genes encoding amyloid precursor protein, presenilin I, and presenilin II; or one having an apolipoprotein E allotype that features one or two epsilon-4 alleles. The subject can also be one having a subclinical *Bordetella pertussis* colonizing infection.

As used herein, the phrase "*Bordetella pertussis* clinical infection" or "BP clinical infection" means a symptomatic BP infection characterized by paroxysms of many rapid coughs which can be followed by a high pitched "whoop" sound. As used herein, the phrase "subclinical *Bordetella pertussis* colonizing infection" or "subclinical BP colonizing infection" means an asymptomatic or mildly symptomatic BP infection (e.g., transient cough or rhinorrhea) that does not feature paroxysms of many rapid coughs which can be followed by a high pitched "whoop" sound.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DESCRIPTION OF THE DRAWINGS

FIG. 1 is a schematic image showing an experimental protocol for assessing the effect of BP infection and/or vaccination with a live, attenuated strain of BP in APP/PS1 mice.

FIG. 2 is a graph showing hippocampal plaque areas in APP/PS1 mice following the protocol shown in FIG. 1.

DETAILED DESCRIPTION

Described herein are methods for preventing, treating, or slowing the progression of a neurodegenerative disease such as AD, by preventing or reducing BP clinical infection or subclinical BP colonizing infection of a subject or neutralizing a BP toxin which causes or contributes to the neurodegenerative disease. The below described embodiments illustrate representative examples of these methods. Nonetheless, from the description of these embodiments, other aspects of the invention can be made and/or practiced based on the description provided below.

General Methodology

Methods involving conventional microbiological, immunological, molecular biological, and medical techniques are described herein. Microbiological methods are described in Methods for General and Molecular Microbiology (3d Ed), Reddy et al., ed., ASM Press. Immunological methods are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17th Edition, McGraw-Hill Professional, 2008.

Subjects

The methods described herein are applicable to any subject having, or at risk for developing a neurodegenerative disease such as AD. Diagnosing AD in human patients can be performed by clinical assessment. A "subject at risk for developing AD" is one diagnosed with mild cognitive impairment (MCI), a person at least 65 years old who has had a parent or sibling with AD, a person having a risk gene associated with developing AD (e.g., APOE-ε4), or a person having a deterministic gene associated with developing AD (e.g., a gene encoding a mutant amyloid precursor protein, presenilin-1, or presenilin-2). Other subjects who might be treated as described herein are those diagnosed with subclinical BP colonizing infection or BP clinical infection, and/or those at risk of acquiring a subclinical BP colonizing infection. The methods described herein are also applicable to subjects having tau tangles and/or beta amyloid plaques.

Agents which Prevent or Reduce BP Subclinical Colonizing Infection

To prevent or treat AD, a subject can be administered an agent which prevents or reduces clinical BP infection or subclinical BP colonizing infection. The agent can be a BP vaccine that induces potent mucosal immunity against BP such as a vaccine including the live attenuated BPZE1 strain described in U.S. Pat. No. 9,119,804, or derivatives thereof such as the adenylate cyclase deficient BPAL10 strain described in U.S. Pat. No. 9,655,959; the fusion protein-expressing BP strains described in U.S. Pat. No. 9,528,086; the serotype 3 fimbrae-expressing BP strains described in WO2019077028A1; the pertactin-deficient BP strains described in U.S. Pat. No. 10,682,377; and the BP strain deficient in adenylate cyclase catalytic domain activity described in WO2020/049133A1. Other suitable attenuated BP strains might be used as the agent. Attenuation might be achieved by mutating a BP strain to reduce its production of one or more (e.g., 1, 2, 3, 4, 5 or more) of the following: pertussis toxin (PTX), dermonecrotic toxin (DNT), tracheal cytotoxin (TCT), adenylate cyclase (AC), lipopolysaccharide (LPS), filamentous hemagglutinin (FHA), pertactin, or any of the bvg-regulated components. Methods for making such mutants are described herein and in U.S. Pat. No. 9,119,804 and U.S. patent application Ser. No. 15/472,436. The agent can also be an antibiotic (e.g., an intranasal antibiotic) which can clear or prevent subclinical *Bordetella pertussis* infections, clinical *Bordetella pertussis* infection, or whooping cough. The antibiotic can, for example be, erythromycin, clarithromycin, or azithromycin.

Agents which Neutralize a BP Toxin

To prevent or treat AD, a subject can be administered an agent which targets and neutralizes one or more BP toxins (e.g., *Bordetella pertussis* toxin). Such agents can be antibodies that specifically bind an antigen expressed by *Bordetella pertussis* bacteria, or vaccines which induce the production of such antibodies.

Formulations/Dosage/Administration

The BP strains described above can be formulated as a vaccine for administration to a subject. A suitable number of live bacteria are mixed with a pharmaceutically suitable excipient or carrier such as phosphate buffered saline solutions, distilled water, emulsions such as an oil/water emulsions, various types of wetting agents, sterile solutions and the like. In some cases, the vaccine can be lyophilized and then reconstituted prior to administration. The use of pharmaceutically suitable excipients or carriers which are compatible with mucosal (particularly nasal, bronchial, or lung) administration are preferred for the purpose of exposing the respiratory tract to BP strains. See Remington's Pharmaceutical Sciences, a standard text in this field, and in USP/NF.

When formulated for mucosal administration, each dose of the vaccine can include a sufficient number of live *Bordetella* bacteria to result in a non-virulent subclinical BP colonizing infection of the respiratory tract, e.g., approximately (i.e., +/−50%) $5\times10^5$ to $5\times10^{10}$ bacteria, depending on the weight and age of the mammal receiving it. For administration to human subjects, the dose can include approximately $1\times10^5$, $1\times10^6$, $5\times10^6$, $1\times10^7$, $5\times10^7$, $1\times10^8$, $5\times10^8$, $1\times10^9$, $5\times10^9$, or $1\times10^{10}$ live BP bacteria. The dose may be given once or on multiple (2, 3, 4, 5, 6, 7, 8 or more) occasions at intervals of 1, 2, 3, 4, 5, or 6 days or 1, 2, 3, 4, 5, or 6 weeks, or 1, 2, 3, 4, 5, 6, or 12 months. Generally, sufficient amounts of the vaccine are administered to result in infection and the protective response. Additional amounts can be administered after the induced protective response wanes.

Methods of Eliciting Protective Responses

The vaccines described herein can be administered to a mammalian subject (e.g., a human being) by any suitable method that deposits the bacteria within the vaccine in the respiratory tract. For example, the vaccines may be administered by inhalation or intranasal introduction, e.g., using an inhaler, a syringe, an insufflator, a spraying device, etc. While administration of a single dose of between $1\times10^5$ to $1\times10^9$ (e.g., $1\times10^5$, $5\times10^5$, $1\times10^6$, $5\times10^6$, $1\times10^6$, $5\times10^6$, $1\times10^7$, $5\times10^7$, $1\times10^8$, $5\times10^8$, $1\times10^9$+/−10, 20, 30, 40, 50, 60, 70, 80, or 90%) live bacteria is typically sufficient to induce a protective response, one or more (1, 2, 3, 4, or more) additional booster doses might be administered in intervals of 4 or more days (e.g., 4, 5, 6, or 7 days; or 1, 2 3, 4, 5, 6, 7, or 8 weeks) until a sufficiently protective response has developed. The development of a protective response can be evaluated by methods known in the art such as quantifying *Bordetella*-specific antibody titers and measuring of *Bordetella* antigen-specific T cells responses (e.g., using an ELISPOT assay). Neuroimaging (e.g., functional MRI and positron emission tomography (PET) studies of cerebral metabolism with fluoro-deoxy-d-glucose (FDG) and amyloid tracers such as Pittsburgh Compound-B (PiB)) can be used to evaluate the progression of neurodegeneration. In cases were a vaccine-induced protective response has waned (e.g., after 1, 2, 3, 4, 5, 10 or more years from the last vaccination) a subject may again be administered the vaccine in order to boost the protective response.

EXAMPLES

Example 1—Materials and Methods

APP/PS1 mice transfected with human genes that cause early onset human AD were used in the experiments described below. See, Holcomb et al. Nat. Med., 4:97-100, 1998. These mice form β-amyloid-containing plaque in their brains, including in the hippocampus, as is seen in human AD. Wild-type (WT) mice were used as controls.

BPZE1, a live attenuated intranasal vaccine derived from *Bordetella pertussis*, from which three of its hallmark virulent toxins have been either inactivated or removed was used in the experiments described below. See, U.S. Pat. No. 9,730,995.

Forty WT and forty APP/PS1 8-week old mice were used in the study. They were assigned to the Groups shown in Table 1 below:

TABLE 1

The treatment groups (10 groups, 10 mice/group) are as follows:

| Group | Mice, 8 weeks | BPZE1 pre-BP | BP challenge | BPZE1 post BP | Sacrifice for Pathology/ Assays |
|---|---|---|---|---|---|
| 1 | WT | No | no | no | 64 weeks |
| 2 | APP/PS1 | No | no | no | 64 weeks |
| 3 | WT | 6 and 32 weeks | no | no | 64 weeks |
| 4 | APP/PS1 | 6 and 32 weeks | no | no | 64 weeks |
| 5 | WT | No | 40 weeks | no | 64 weeks |
| 6 | APP/PS1 | No | 40 weeks | no | 64 weeks |
| 7 | WT | 6 and 32 weeks | 40 weeks | no | 64 weeks |
| 8 | APP/PS1 | 6 and 32 weeks | 40 weeks | no | 64 weeks |
| 9 | WT | No | 40 weeks | 44 weeks | 64 weeks |
| 10 | APP/PS1 | No | 40 weeks | 44 weeks | 64 weeks |

The experimental protocol is shown in FIG. 1. Mice were treated with BPZE1 or vehicle at 0 and 2 weeks. At 40 weeks mice were infected with BP or mock infected. At 44 weeks Groups 9 and 10 were again administered BPZE1. At 64 weeks, the hippocampus was removed from each animal and assessed for Aβ plaques using Congo Red staining.

Example 2—Results

Referring to FIG. 2, hippocampal Aβ plaque was assessed by Congo Red staining. The mean plaque area as a percentage of the controls was determined for plaques 21-50, 51-80, 90-120, and >120 pixels in size. Infection with BP alone tended to increase hippocampal area covered by Aβ plaque compared to controls. BPZE1 pre-vaccination reduced hippocampal area covered by Aβ plaque in APP/PS1 mice subsequently exposed to BP, compared with BP exposed mice not pre-vaccinated with BPZE1 (mixed p-value for repeated measures across multiple β-amyloid plaque sizes, 0.003). BPZE1 vaccination reduced hippocampal area coverage with β-amyloid plaque in the combined group of APP/PS1 mice subsequently exposed and not exposed to BP, compared with control mice not exposed to BP (mixed p-value for repeated measures across multiple β-amyloid plaque sizes, 0.001). BPZE1 exhibited a strong trend to reduce the hippocampal area covered by β-amyloid plaque in APP/PS1 mice that have not been exposed to BP, compared with control unvaccinated mice not exposed to BP (mixed p-value for repeated measures across multiple β-amyloid plaque sizes, 0.055).

BPZE1 has protective benefits vs. controls in mice genetically predisposed to produce Aβ brain plaques, as seen in human AD. BPZE1 vaccination significantly reduces Aβ plaque hippocampal coverage in mice subsequently exposed to BP, and is associated with less hippocampal Aβ plaque in the combined group of mice that are subsequently exposed and not exposed to BP.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for preventing or reducing β-amyloid plaque in the brain of a subject having or at risk for developing Alzheimer's disease, the method comprising the step of administering to the subject a composition comprising a live, attenuated *Bordetella pertussis* strain which is able to colonize the subject and induce a protective response in the subject that reduces the amount of β-amyloid plaque that would have formed or would have been present in the brain of the subject if the subject were not administered the composition.

2. The method of claim 1, wherein the live, attenuated *Bordetella pertussis* strain is capable of colonizing infection of the subject's respiratory tract.

3. The method of claim 1, wherein the live attenuated *Bordetella pertussis* strain comprises a mutated pertussis toxin gene, a deleted or mutated dermonecrotic gene, and a heterologous ampG gene which replaces the *Bordetella pertussis* ampG gene.

4. The method of claim 3, wherein the live attenuated *Bordetella pertussis* strain is a BPZE1 strain deposited with the Collection Nationale de Culture Microorganismes (C.N.C.M.) on Mar. 9, 2006, under accession number 1-3585.

5. The method of claim 1, wherein the live attenuated *Bordetella pertussis* strain is non-virulent.

6. The use of claim 1, wherein the subject has been diagnosed with Alzheimer's disease.

7. The method of claim 1, wherein the subject has been diagnosed with mild cognitive impairment.

8. The method of claim 1, wherein the subject has mutations in at least one selected from the group consisting of genes encoding amyloid precursor protein, presenilin I, and presenilin II.

9. The method of claim 1, wherein the subject has an apolipoprotein E allotype that features one or two epsilon-4 alleles.

10. The method of claim 1, wherein the subject has a subclinical *Bordetella pertussis* infection.

* * * * *